United States Patent
Bosse-Platiere et al.

(10) Patent No.: US 10,892,054 B2
(45) Date of Patent: Jan. 12, 2021

(54) CONTROL STATION FOR OUTPUTTING INFORMATION RELATING TO A MULTIPLICITY OF INFUSION SYSTEMS TO A USER

(71) Applicant: Fresenius Vial SAS, Brézins (FR)

(72) Inventors: Didier Bosse-Platiere, Les Abrets (FR); Veronique Delfosse, Vourles (FR)

(73) Assignee: Fresenius Vial SAS, Brézins (FR)

( * ) Notice: Subject to any disclaimer, the term of this patent is extended or adjusted under 35 U.S.C. 154(b) by 0 days.

(21) Appl. No.: 16/461,868

(22) PCT Filed: Nov. 17, 2017

(86) PCT No.: PCT/EP2017/079563
§ 371 (c)(1),
(2) Date: May 17, 2019

(87) PCT Pub. No.: WO2018/104029
PCT Pub. Date: Jun. 14, 2018

(65) Prior Publication Data
US 2019/0275246 A1  Sep. 12, 2019

(30) Foreign Application Priority Data

Dec. 6, 2016  (EP) .................................... 16306621

(51) Int. Cl.
*G16H 40/60* (2018.01)
*G16H 40/63* (2018.01)
(Continued)

(52) U.S. Cl.
CPC ............ *G16H 40/63* (2018.01); *A61M 5/172* (2013.01); *G06F 19/3418* (2013.01);
(Continued)

(58) Field of Classification Search
CPC ...... A61M 5/14; A61M 5/142; A61M 5/1424; A61M 5/172; G06F 19/00; G06F 19/34;
(Continued)

(56) References Cited

U.S. PATENT DOCUMENTS 8,612,257 B2 * 12/2013 Zaitsu ................. A61M 5/1413
705/3
8,858,526 B2   10/2014 Blomquist
(Continued)

OTHER PUBLICATIONS

International Search Report and Written Opinion, counterpart International Appl. No. PCT/EP2017/079563 (dated Feb. 12, 2018) (13 pages).

*Primary Examiner* — Van T Trieu
(74) *Attorney, Agent, or Firm* — Cook Alex Ltd.

(57) ABSTRACT

A control station for outputting information relating to a multiplicity of infusion systems to a user includes a data collection section being operatively connectable to a multiplicity of infusion systems via a communication network for receiving data from the infusion systems, an output section for outputting information relating to the multiplicity of infusion systems, and a processing section configured to process data received from the infusion systems. The processing includes relating data received from an infusion system to a status class of a multiplicity of predefined status classes to obtain a status indication for the infusion system, and transmitting the status indication to the output section for outputting the status indication to a user.

10 Claims, 4 Drawing Sheets

(51) Int. Cl.
  *A61M 5/172* (2006.01)
  *G06F 19/00* (2018.01)
  *G16H 40/40* (2018.01)

(52) U.S. Cl.
  CPC ......... *G06F 19/3468* (2013.01); *G16H 40/40* (2018.01); *G16H 40/60* (2018.01); *A61M 2205/3561* (2013.01); *A61M 2205/502* (2013.01)

(58) Field of Classification Search
  CPC .. G06F 19/3468; G05B 19/042; G16H 20/17; G16H 40/67
  See application file for complete search history.

(56) References Cited

U.S. PATENT DOCUMENTS

| | | | |
|---|---|---|---|
| 9,501,619 B2 * | 11/2016 | Portnoy | G06F 19/325 |
| 10,157,266 B2 * | 12/2018 | Dudar | G06F 19/3468 |
| 2002/0013551 A1 * | 1/2002 | Zaitsu | A61M 5/1413 604/151 |
| 2007/0253021 A1 | 11/2007 | Mehta et al. | |
| 2009/0270833 A1 * | 10/2009 | DeBelser | A61M 5/16831 604/500 |
| 2011/0072379 A1 | 3/2011 | Gannon et al. | |
| 2011/0107251 A1 | 5/2011 | Guaitoli et al. | |
| 2012/0011253 A1 | 1/2012 | Friedman et al. | |

* cited by examiner

CONTROL STATION FOR OUTPUTTING INFORMATION RELATING TO A MULTIPLICITY OF INFUSION SYSTEMS TO A USER

The present application is a U.S. National Stage of PCT International Patent Application No. PCT/EP2017/079563, filed Nov. 17, 2017, which claims priority to EP Application No. 16306621, filed Dec. 6, 2016, both of which are hereby incorporated herein by reference.

BACKGROUND

The invention relates to a control station for outputting information relating to a multiplicity of infusion systems to a user according to the preamble of claim 1 and to a method for outputting information relating to a multiplicity of infusion systems to a user.

A control station of this kind comprises a data collection section being operatively connectable to a multiplicity of infusion systems via a communication network for receiving data from the infusion systems, and an output section for outputting information relating to the multiplicity of infusion systems.

Infusion systems are used in a healthcare environment for providing infusions to patients. Herein, in a care area, for example in a ward or in an intensive care unit (ICU) of a hospital, at the bedside of a patient a multiplicity of infusion devices such as syringe infusion pumps or volumetric (peristaltic) infusion pumps may be organized on a rack to form an infusion system. Using the infusion system, medical fluids such as medication or nutritional fluids may be administered to the patient.

Infusion systems of this kind are typically connected to a hospital communication network to communicate data with a central station, such data also including clinical context, nurse programmed data, fluid delivery data and infusion alert status. In this way, operational data such as for example drug library data may be transmitted from the central server to the infusion system, and during an ongoing infusion operation data may be transmitted from the infusion system to the central server, such data for example also including information relating to alarm conditions or the like which require attention of a user, in particular a nurse.

Within a care area in a hospital environment, for example in a ward of a hospital, a central control station may be placed in a central area such that a nurse may centrally monitor data relating to infusion systems in different rooms on a screen of the control station. Herein, infusion systems output various kinds of information relating to alarm conditions of high priority or low priority, to operational parameters, to functional states or to general information, which are all displayed to the user and which must be analyzed by the user in order to determine if and possibly what action may be required. To perform an action, the user must then attend to the concerned infusion system at the bedside of the patient, wherein the user may be required to visit one infusion system after another to sequentially perform all actions that are currently required.

Herein, it must be considered that nowadays the number of patients to be taken care of by a nurse is large, and in addition the amount of data output by infusion systems is large, such that a nurse must be able to cope with a large amount of information and must be able to identify relevant information from information having a reduced priority.

There hence is a desire to support a nurse in identifying relevant information. In particular, it is essential that a nurse is able to efficiently identify information that is relevant, which ultimately may help to reduce alarm fatigue and may allow the nurse to react more quickly.

In addition, it is a desire to support a user, in particular a nurse, to be able to localize unused infusion devices. Nowadays, a user, in particular a nurse, spends a substantial amount of time with localizing infusion devices prior to setting up an infusion operation. If localization of infusion devices becomes more apparent to a user, this may help to improve the workflow of a user.

U.S. Pat. No. 8,858,526 B2 discloses a method of programming a medical infusion pump in which a first menu containing a plurality of therapy menu items are displayed. The therapy menu items each correspond to a therapy.

US 2011/0107251 A1 discloses a user interface for monitoring the status of medical machines. The user interface includes a display which shows data coming from a processing unit relating to parameters of the machines. The processing unit comprises means for establishing to which operating status of the medical machines the data belongs to. The processing unit determines if a medical machine is in a correct functioning status; if a medical machine is in a warning status; or if a machine is in a critical status. Means generate synthetic data characterized by colors according to whether the medical machine is in the correct functioning, the warning or the critical status.

It is an object of the instant invention to provide a control station, a care system comprising a control station and a method for outputting synthetized generic information relating to a multiplicity of infusion systems which may allow to improve a workflow for a user, in particular a nurse, by supporting a user to identify relevant information relating to an infusion system.

SUMMARY

This object is achieved by means of a control station comprising the features of claim 1.

Accordingly, the control station comprises a processing section being constituted to process data received from the infusion systems, wherein the processing includes:
  relating data received from an infusion system to a status class of a multiplicity of predefined status classes to obtain a status indication for the infusion system, and
  transmitting the status indication to the output section for outputting the status indication to a user.

The data may be received from the data collection section in real-time, i.e. without any substantial delay, and may be processed by the processing section in real-time to determine the status indication. The status indication hence represents and corresponds to an actual status of an infusion system to which the data relates.

The data collection section, the processing section and the output section are all components of the control station. The data collection section, the processing section and the output section may for example be implemented by software and not necessarily are constituted as separate (hardware) components. In a system architecture organized by layers, the data collection section, the processing section and the output section may for sample be implemented by separate layers between which data is transferred back and forth such that, for sample, the data collection section passes data to the processing section, which passes data to the output section.

The data collection section serves to collect data from a multiplicity of infusion systems. An infusion system may be a single infusion device such as a syringe infusion pump or a volumetric (peristaltic) infusion pump. In a more complex set up, an infusion system may be an arrangement comprising multiple infusion devices such as syringe pumps and/or volumetric pumps, which are organized on an organization device such as a rack. The infusion devices are connected to a communication network, for example an intranet network of a hospital, wherein an organization device, such as a rack, on which the infusion devices are organized, i.e. mechanically held and electrically connected, may serve as a communication link such that infusion devices organized on the organization device communicate via the organization device and via the communication network with the data collection section of the control station.

The processing section serves to process data received from the infusion systems to synthesize generic data from the data received. Herein, within the processing, data received from an infusion system is associated with a status class from a number of different, predefined status classes, and in this way a status indication for the infusion system to which the data relates is determined. This status indication may then be output to a user by means of the output section, which may for example comprise a display device such that the status indication may be displayed to a user.

The predefined status classes may correspond to different priorities. If an infusion system is found to be in a status class of high priority, a corresponding status indication is output to the user such that the user, in particular a nurse, is immediately made aware of the status of the infusion system. Different status classes of different priorities herein may be associated with different colors for the displaying on the display device of the output section. A status class of a high priority may be indicated for example by the color red, whereas a status class of a medium priority may be indicated by the color orange/yellow, and a status class of a low priority may be indicated by the color green.

Via the output section, hence, information may be displayed in a nurse-action oriented way. By relating the data received from the infusion systems to predefined status classes having different priorities, a user is immediately made aware of a potential action to be taken at an infusion system and its priority. The user hence can adjust his/her workflow depending on the priority of actions to be performed.

An infusion system is typically arranged at the bedside of a patient. A status indication herein may indicate a status for the entire infusion system comprising multiple infusion devices for example organized on an organization device such as a rack. A status indication indicating a high priority and hence requiring immediate attention at the infusion system hence may tell the user that on at least one of the infusion devices of the infusion system an immediate action is required.

A status indication may, alternatively, relate to a single infusion device of a multiplicity of infusion devices of an infusion system. In this case for each infusion device of an infusion system a separate status indication is displayed.

A status indication may also relate to slots of an organization device, for example a rack, of an infusion system, the status indication for example stating whether a slot is empty or not.

In one embodiment, a first status class may indicate that a short-term, immediate user action is required at an infusion system. The first status class may for example be triggered by an alarm condition on an infusion device, such as an occlusion alarm or an end-of-infusion alarm. The first status class may furthermore be triggered if an infusion device is in a disconnected state or if a communication error occurs.

A second status class may indicate that a mid-term user action is required at an infusion system, i.e., an action which does not need to be performed immediately, but with a medium priority. The second status class may for example be triggered if an infusion device is in a prealarm state, for example due to a low battery state. The second status class may also be triggered if for example it is found that a user action, such as the programming of the infusion device, has not been completed by the user.

A third status class may indicate that no user action is required at an infusion system while an infusion operation is in progress. The third status class may be triggered if it is found that an ongoing infusion operation runs normally, without the presence of an alarm condition. A pump hence is in a user delivery mode, for example corresponding to a continuous infusion, a ramp-up state, a sequential infusion, a bolus administration or the like.

A fourth status class may indicate, in a further embodiment, that a user action is in progress at an infusion system. This fourth status class, if displayed on the control station, indicates that a user is currently present at the infusion system such that no further user is required to pay attention to the infusion system. The fourth status class may for example be triggered if an installation currently is in progress, if a programming of an infusion device is in progress or the like.

A fifth status class may indicate that at least one infusion device of an infusion system is available for use on another patient. This first status class may be triggered if an infusion device is switched off. This fifth status class may indicate to a user that an infusion device is available for use on another patient, such that a free to use infusion device is localized to a user and may easily be found for installation at another patient.

A sixth status class may indicate that no user action is required at an infusion system while no infusion operation is in progress. This sixth status class may for example be triggered for an empty slot of an organization device of an infusion system.

In one embodiment, the processing section is constituted to create, from the received data, an aggregated database in which data relating to an infusion system is stored. In the database, current information relating to infusion devices of an infusion system are stored and correlated with each other. The database serves to identify and synchronize information relating to infusion devices of an infusion system, which is beneficial because not all information may arrive at the control station at the same time and at a similar transmission rate.

For example, some data may be transferred from infusion devices of an infusion system in a cyclic fashion. Within a cyclic data transmission data is transmitted periodically with predefined gaps in between transmission bursts.

Another transmission mode may be an event-based data transmission mode, in which infusion devices of an infusion system transmit data in a spontaneous fashion once a predefined event occurs. For example, if an alarm condition arises, data relating to that alarm condition may immediately be transferred from the concerned infusion device to the control station.

In yet another transmission mode, data may be transmitted from infusion devices of an infusion system in reply to a request from the control station. In a periodic or aperiodic fashion the control station may request data from an infusion system, in response to which messages are sent from the infusion system to the control station.

Within the aggregated database, incoherent data may be correlated such that it is defined what data are current for an infusion device of an infusion system.

The processing section may be constituted to receive and process data of different data groups. In a first data group data relating to a connection/disconnection status of an infusion system may be obtained. In a second data group data relating to alarm conditions of an infusion system may be obtained. And in a third data group data relating to infusion information of infusion operations of infusion devices may be obtained. The processing section herein, in one embodiment, may be set up to combine data of different data groups to determine the status indication. For example, the processing section may determine whether an infusion operation is currently ongoing on an infusion device, which may be derived from data cyclically received from the infusion device. If now an alarm condition arises and corresponding data is received at the control station by spontaneous, event-based data transmission, the processing section may correlate the infusion operation status and the alarm condition to determine a high priority status indication for the infusion device.

A care system may comprise a multiplicity of infusion systems, for example arranged at the bedside of different patients. Each infusion system herein may comprise one or multiple infusion devices such as syringe infusion pumps and/or volumetric (peristaltic) infusion pumps. Infusion devices serve to administer medical fluids to a patient, such as medication or nutritional fluids. The care system may comprise a control station of the kind described above, the control station for example being placed in a central location of a care area such that the control station allows for a central monitoring of ongoing infusion operations on the multiple infusion systems.

The control station may for example be linked to the multiplicity of infusion systems via a communication network such as a hospital intranet making use of a TCP/IP protocol.

The object is also achieved by a method for outputting information relating to a multiplicity of infusion systems to a user, the method comprising:
  using a data collection section of a control station, receiving data from multiplicity of infusion systems being operatively connected via a communication network to the data collection section, and
  outputting information relating to the multiplicity of infusion systems using an output section.
Herein, a processing section processes data received from the infusion systems, wherein the processing includes:
  relating data received from an infusion system to a status class of a multiplicity of predefined status classes to obtain a status indication for the infusion system, and
  transmitting the status indication to the output section for outputting the status indication to a user.

The advantages and advantageous embodiments described above for the control station and the care system equally apply also to the method, such that it shall be referred to the above.

BRIEF DESCRIPTION OF THE DRAWINGS

The idea of the invention shall subsequently be described in more detail with respect to the embodiments shown in the figures. Herein.

DETAILED DESCRIPTION OF THE EMBODIMENTS

Figure 1:
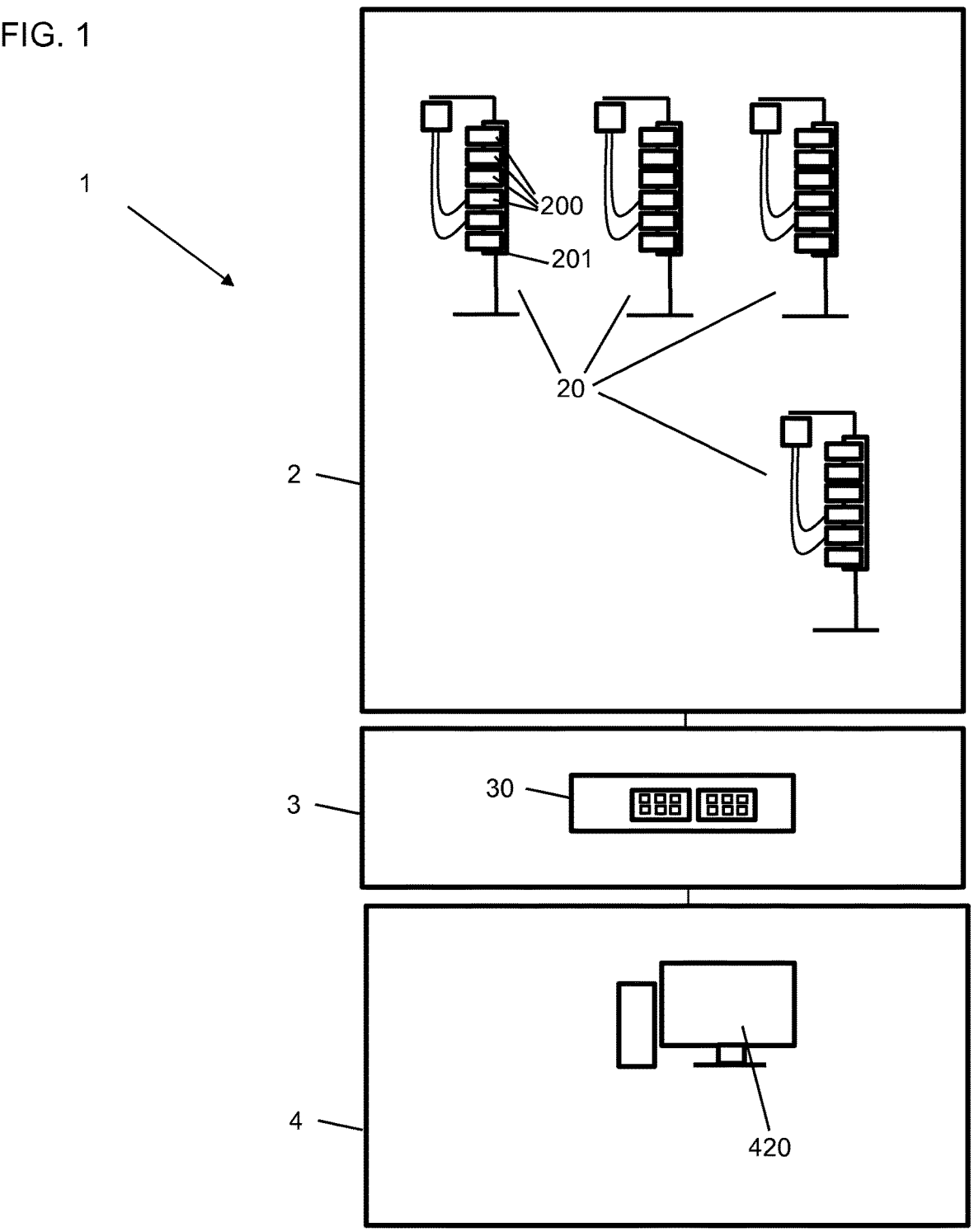
FIG. 1 shows a schematic drawing of a care system comprising multiple infusion systems in a care area, a communication network, and a control station.

FIG. 1 shows a schematic view of a care system 1 as it can be found for example in a hospital environment.

Within the care system 1, in a care area 2, for example a ward of a hospital or an intensive care unit of a hospital, a multiplicity of infusion systems 20 may be arranged at the bedside of various patients to perform infusions to the patients to administer medical fluids such as medication or a nutritional fluids or the like to the patients.

Herein, each infusion system 20 may comprise a multiplicity of infusion devices 200 such as syringe pumps or volumetric (peristaltic) infusion pumps, which are organized on an organization device 201 in the shape of a rack to form a vertical stack of the infusion devices 200. Via the infusion devices 200, different fluids may be administered to the patient at the same time or in a sequential manner.

The infusion devices 200 are mechanically held on the organization device 201 and also are electrically connected to the organization device 201. The organization device 201 may for example provide a power supply to the infusion devices 200 and may also serve as a communication link via which the communication devices 200 are connected to a hospital communication network 3 having for example a hub 30 providing for data connections in between various different devices.

Via the hospital communication network 3 the infusion systems 20 are in communication connection with a central control station 4, which may be arranged for example in a central area of the care area 2, such as in a central nurse room.

Figure 2:
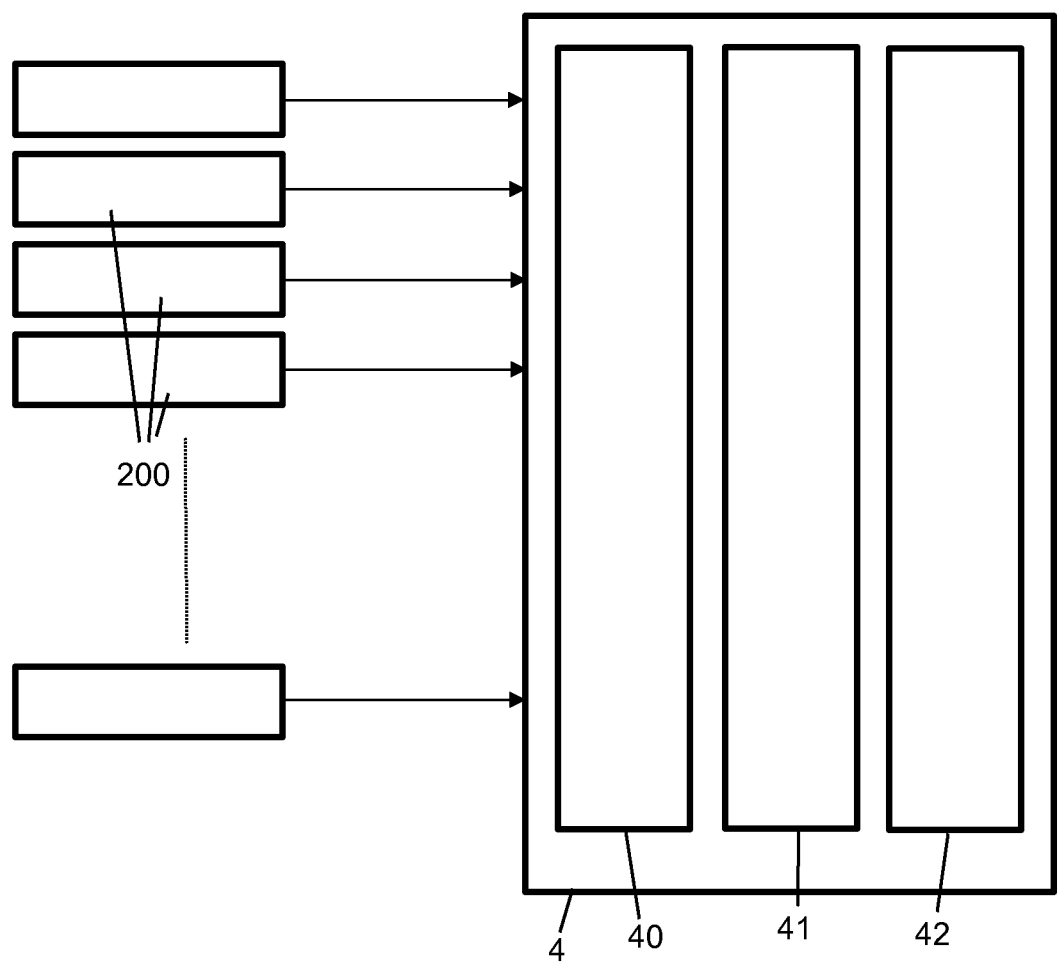
FIG. 2 shows a schematic view of the control station in connection with infusion devices of infusion systems.

The control station 4, in one embodiment, has an architecture as it schematically is shown in FIG. 2. The control station 4 may be organized by layers, a first layer constituting a data collection section 40, a second layer constituting a processing section 41 and a third layer constituting an output section 42, to which for example also a display device 420, as is schematically shown in FIG. 1, belongs.

The data collection section 40 serves to collect data from a multiplicity of infusion devices 200 of multiple infusion systems 20 distributed throughout the care area 2. The data collection section 40 passes received data on to the processing section 41, which processes the data and provides processed data to the output section 42 for outputting to a user by displaying processed data on the display device 420.

The processing section 41 of the control station 2 is in particular set up and configured to process data received from the infusion devices 200 of the infusion systems 20 by relating the data to a status class out of a multiplicity of predefined status classes.

In one embodiment, different status classes associated with different priorities may exist, as listed in the subsequent table:

TABLE 1

| Status class | Priority | Color | Information to nurse |
|---|---|---|---|
| 1 | High | Red | The nurse needs to organize a short-term action at the bedside |
| 2 | Medium | Orange | The nurse needs to organize a mid-term action at the bedside |
| 3 | Information | Green | No nurse action is needed at the bedside: pump(s) with a fluid delivery in progress |
| 4 | Information | Blue | a nurse action is in progress at the bedside |
| 5 | Information | White | The nurse can use available pump(s) for another patient |
| 6 | Information | Grey | No nurse action needed at the bedside: no running infusion |

A first status class may indicate that a short-term action at the bedside of a patient is required. A second status class may indicate that a mid-term action is required at the bedside of a patient. A third status class may indicate that no nurse action is currently required at the bedside of a patient while an infusion process is ongoing. A fourth status class may indicate that a nurse action currently is in progress at the bedside of a patient, because a nurse for example is currently programming an infusion device or is installing a syringe on a syringe pump. A fifth status class may indicate that a pump is available for installation on another patient. And a sixth status class may indicate that no nurse action is required at the bedside of a patient while no infusion is ongoing.

The status classes, in one embodiment, are associated with different priorities and different colors. In Table 1, the status classes 1 and 2 are related to a high priority respectively a medium priority and require an immediate respectively a mid-term nurse action. The other status classes refer to information provided to the nurse. From the data received from an infusion device 200 of an infusion system 20 it is determined into which status class the infusion device 200 falls, and accordingly a status indication for the infusion device 200 is determined which then is displayed on the display device 420 of the output section 42. The status indication is represented by the color. If it for example is found that the infusion device 200 falls into the first status class, correspondingly the color red is displayed for the infusion device 200 on the display device 420 of the output section 42.

The different status classes are triggered depending on certain conditions.

For example, the first status class may be triggered if the data received from an infusion device 200 indicates that an infusion operation currently is ongoing at the infusion device 200 and a critical alarm condition, such as an occlusion alarm or an end-of-infusion alarm, arises. If the data received from the infusion device 200 indicates that these conditions are fulfilled, it is found that the infusion device 200 should be assigned to the first status class, and correspondingly the color red is displayed on the display device 420 for the infusion device 200. The nurse hence is immediately made aware that an immediate action is required at this particular infusion device 200.

The second status class may for example be triggered if the data received from an infusion device 200 indicates that an infusion process is ongoing at the infusion device 200 and an alarm condition of a low or medium priority arises, such as a pre-alarm in case of a low battery status at the infusion device 200. In this case the second status class is assigned to the infusion device 200, and the color orange is displayed on the display device 420 of the output section 42 for this particular infusion device 200. The nurse hence is made aware that an action at the infusion device 200 is necessary with a medium priority.

The third status class may for example be triggered if it is determined at an infusion device 200 that an infusion process is ongoing in a regular fashion, with no severe alarm conditions being present. In this case the third status class is assigned to the infusion device 200, and the color green is displayed on the display device 420, such that the nurse is made aware that no action is required at this particular infusion device 200.

The fourth status class may for example be triggered if an installation or programming is in progress at an infusion device 200. In this case it can be assumed that a nurse is currently present at the infusion device 200. In this case the infusion device 200 is assigned to the fourth status class, and the color blue is displayed on the display device 420. A nurse monitoring the control station 4 hence knows that a nurse is present at the infusion system 20 and hence knows that no action from her is required at the infusion system 20.

The fifth status class may be triggered for example if an infusion device 200 is switched off. In this case the fifth status class is assigned to the infusion device 200, and the color white is displayed for the particular infusion device 200 on the display device 420. In this case the nurse is made aware that the infusion device 200 may be used for another patient. This greatly helps a nurse to identify free infusion devices 200 without great effort to localize such infusion devices 200, which helps to improve the workflow of a nurse.

The sixth status class may be triggered for example if it is found that a slot of an organization device 201 in the shape of a rack currently is empty. For such an empty slot the sixth status class may be assigned and the color gray may be displayed on the display device 420.

Data may be transmitted from the infusion devices 200 to the control station 2 in different fashions. For example, some data may be transmitted in a cyclic fashion, whereas other data may be transmitted in an event-based, spontaneous fashion, and yet other data may be transmitted in a request/reply scheme. For example, data relating to an ongoing infusion operation may be transmitted in a cyclic transmission scheme, in which data messages are sent with periodic gaps in between transmission bursts. Using an event-based transmission scheme, data is immediately transmitted in case a certain event occurs. For example, if an occlusion alarm is present, such data is immediately transferred to the control station 4. Within the request/reply transmission mode the control station 4 may request an infusion device 200 to provide certain data, to which the infusion device 200 replies by a suitable message.

Within the processing section 41 of the control section 2, data received from infusion devices 200 may be stored in an aggregated database. For determining into which status class an infusion device 200 currently falls, different data herein may be combined and analyzed. For example, the first status class may be assigned to an infusion device 200 if a first set of data for example received by cyclic data transmission indicates that an infusion process is ongoing and a second set of data received by spontaneous, event-based data transmission indicates that a high priority alarm, for example an occlusion alarm, has occurred on the infusion device 200.

Different data of different data groups herein may be stored in the aggregated database. For example, a first data group may correspond to data indicating a connection/disconnection status of an infusion device 200. A second data group may correspond to pump alerts. And a third data group may indicate pump infusion information.

Figure 4:
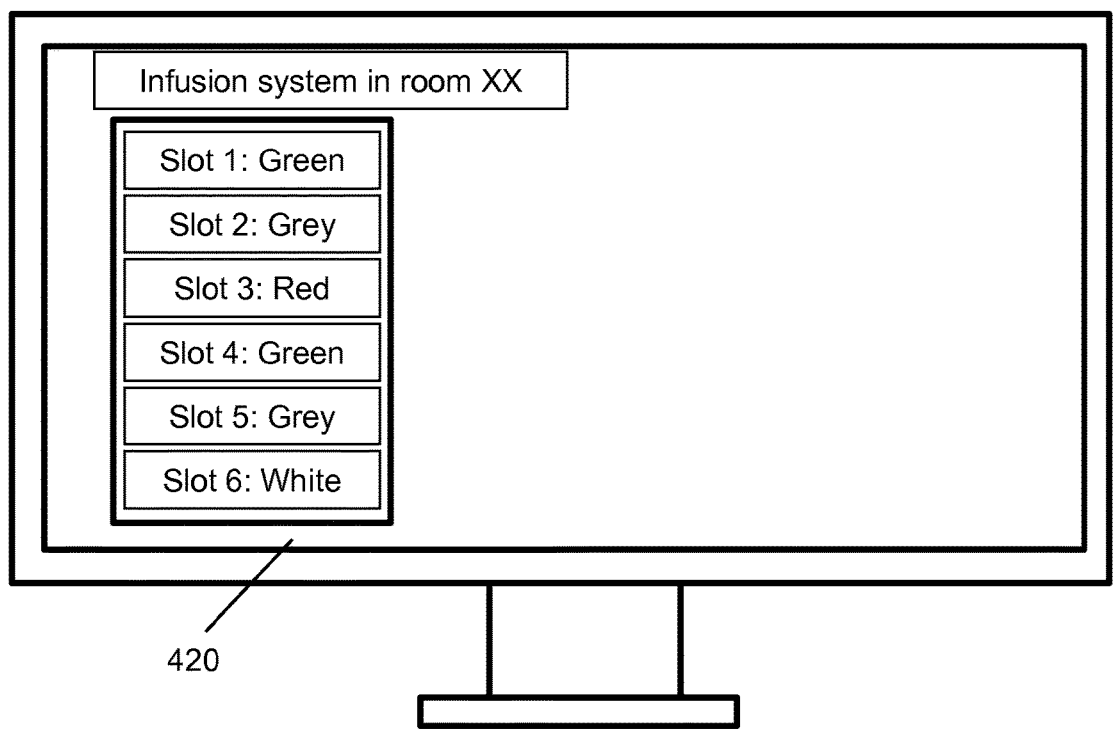
FIG. 4 shows an example of a screen view of the control station.

Generally, a status indication may be displayed for an entire infusion system 200. Beneficially, however, on the display device 420 of the output section 42 a status indication is displayed for each infusion device 200 installed on an organization device 201 of an infusion system 20. For example, a status indication may be displayed for each slot of an organization device 201, as illustrated in FIG. 4, indicating into which status class an infusion device 200 in a particular slot of the organization device 201 currently falls by displaying a suitable color.

By displaying a status indication for infusion systems 20 centrally on the control station 4, a nurse is enabled to efficiently monitor multiple infusion systems 20 at the same time. Herein, the data is processed such that the nurse is presented with information in a nurse-action oriented way. In particular, the nurse is immediately made aware of an action that potentially may be required at an infusion system 20 and may adjust her workflow to perform actions throughout a care area 2 accordingly.

Figure 3:
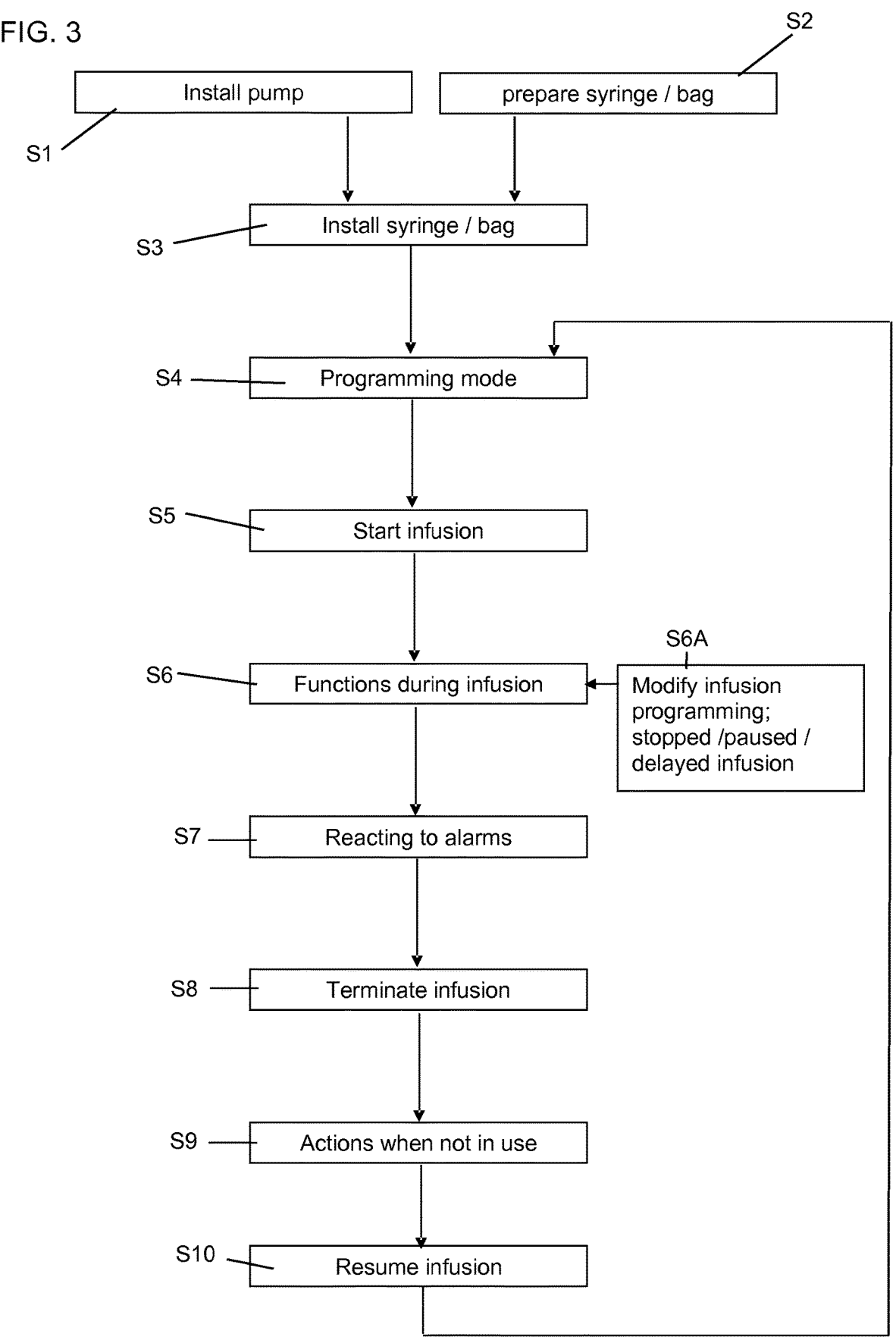
FIG. 3 shows a schematic workflow for operating infusion devices.

An example workflow for performing an infusion operation is illustrated in a flow chart in FIG. 3.

Prior to starting in infusion, the infusion device 200 may be switched off. In that case the color gray relating to the sixth status class may be displayed for the infusion device 200.

If, when switching on the pump, it for example is found that the pump is not compatible or is in an unknown mode or a communication error occurs, the color red may be displayed for the pump, corresponding to the first status class.

During her regular workflow for performing an infusion, the nurse starts with installing a pump at the bedside of a patient (step S1) and prepares a syringe (in case of a syringe pump) or an infusion bag (in case of a volumetric infusion pump) (step S2).

In step S3 the syringe or the infusion bag are installed on the infusion device 200. During installation, the color blue may be displayed for the infusion device 200 on the control station 2, indicating that an installation is currently ongoing at the infusion device 200. If during installation it is found that a technical error exists or the device has run out of battery, the color red may be displayed for the infusion device, corresponding to the first status class.

In step S4, the nurse programs the infusion device 200 for performing the infusion operation, for example by setting a dose rate, an infusion volume and the like. Again, the color blue may be displayed for the infusion device 200, because a programming is ongoing at the infusion device 200. If an error is found, the status red may be displayed. If the programming action has been started, but not completed, eventually the color orange may be displayed for the infusion device 200, indicating that a midterm action is required at the infusion device 200.

In step S5, the infusion is started and carried out. In step S6 functions may be initiated during the infusion, for example to modify the infusion programming, to stop an infusion, to pause an infusion or to delay an infusion, as indicated in step S6A. Also, during an infusion operation alarms may occur, which in step S7 may be reacted to. In step S8 an infusion may be terminated. During all these steps the color green may be displayed, if the infusion operation proceeds without major issues. If a high priority alarm occurs, the color red may be displayed for the infusion device 200. If a prealarm occurs, for example due to a low battery, the color orange maybe be displayed for the infusion device 200. And if the infusion device 200 in step S6 is paused or delayed, the color blue may be displayed.

After termination, the infusion device 200 may be switched off, in case of which the color gray may be displayed for the infusion device 200.

Step S9 indicates actions that may be done when an infusion device 200 is not in use. In step S10, an infusion operation may be resumed, upon which the process starts anew at step S4.

When an infusion operation is running regularly (green color), the processing section 41 receives data relating to the infusion operation and processes them for a generic display on the display device 420. The processed data herein may be formatted according to the IPEC profile (infusion profile event communication), which allows to push data to other external systems which are compatible with IPEC.

In another example, the control station 41 may compute the remaining time of an infusion operation according to the programming mode and the delivery mode, wherein on the control station 41 the overall remaining time and also the remaining time until a change of syringes/bags in case of a sequential infusion using multiple syringes/bags may be displayed.

The idea underlying the invention may be implemented in an entirely different fashion.

In particular, different status classes may exist, wherein the number of status classes may be smaller than 6 or larger than 6. Also, status indications may be displayed by color or in any other suitable way, for example by text messages or by sound.

LIST OF REFERENCE NUMERALS

1 Care system
2 Care area
20 Infusion system
200 Infusion device
201 Organization device (rack)
3 Hospital communication network
30 Hub
4 Central control station
40 Data collection section
41 Processing section
42 Output section
420 Display device

The invention claimed is:

1. A control station for outputting information relating to a multiplicity of infusion systems to a user, the control station comprising:
   a data collection section being operatively connectable to a multiplicity of infusion systems via a communication network for receiving data from the infusion systems,
   an output section for outputting information relating to the multiplicity of infusion systems, and
   a processing section configured to process data received from the infusion systems, wherein the processing includes:
      relating data received from an infusion system to a status class of a multiplicity of predefined status classes to obtain a status indication for the infusion system,
      a first status class indicating that a short-term user action is required at an infusion system, a second status class indicating that a mid-term user action is required at an infusion system, and a third status class indicating that no user action is required at an infusion system while an infusion operation is in progress, and transmitting the status indication to the output section for outputting the status indication to a user, wherein the processing section is configured to combine data of different data groups to determine the status indication.

2. The control station according to claim 1, wherein the output section comprises a display device for displaying the status indication.

3. The control station according to claim 2, wherein different status indications are displayed in different colors.

4. The control station according to claim 1, wherein a fourth status class indicates that a user action is in progress at an infusion system, a fifth status class indicates that at least one infusion device of an infusion system is available for use on another patient, and/or a sixth status class indicates that no user action is required at an infusion system while no infusion operation is in progress.

5. The control station according to claim 1, wherein the processing section is configured to create, from the received data, an aggregated database in which data relating to an infusion system is stored.

6. The control station according to claim 1, wherein the data collection section is configured to receive data from the multiplicity of infusion systems by cyclic data transmission for which an infusion system cyclically transmits data, by event-based data transmission for which an infusion system transmits data in case a predefined event occurs at the infusion system, and/or by data transmission from an infusion system in reply to a request by the control station.

7. The control station according to claim 1, wherein the processing section is configured to receive data associated with a first data group relating to a connection/disconnection status of an infusion system, a second data group relating to alarm conditions of an infusion system, and/or a third data group relating to infusion information of infusion operations of an infusion system.

8. A care system applicable in a healthcare environment, comprising a multiplicity of infusion systems, each infusion system comprising at least one infusion device for administering a medical fluid to a patient, and a control station according to claim 1.

9. The care system according to claim 8, wherein the control station is connected to the multiplicity of infusion systems via a communication network.

10. A method for outputting information relating to a multiplicity of infusion systems to a user, the method comprising:

using a data collection section of a control station, receiving data from multiplicity of infusion systems being operatively connected via a communication network to the data collection section, and outputting information relating to the multiplicity of infusion systems using an output section, using a processing section, processing data received from the infusion systems, wherein the processing includes:

relating data received from an infusion system to a status class of a multiplicity of predefined status classes to obtain a status indication for the infusion system, a first status class indicating that a short-term user action is required at an infusion system, a second status class indicating that a mid-term user action is required at an infusion system, and a third status class indicating that no user action is required at an infusion system while an infusion operation is in progress, and transmitting the status indication to the output section for outputting the status indication to a user, wherein the processing section is configured to combine data of different data groups to determine the status indication.

* * * * *